US012658321B2

(12) United States Patent
Lee et al.

(10) Patent No.: US 12,658,321 B2

(45) Date of Patent: Jun. 16, 2026

(54) TOOTH EXTRACTION DIFFICULTY DIAGNOSIS AND COMPLICATIONS PREDICTION DEVICE AND METHOD

(71) Applicant: GWANGJU INSTITUTE OF SCIENCE AND TECHNOLOGY, Gwangju (KR)

(72) Inventors: Kyoobin Lee, Gwangju (KR); Junseok Lee, Gwangju (KR); Jumi Park, Gwangju (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 239 days.

(21) Appl. No.: 18/380,445

(22) Filed: Oct. 16, 2023

(65) Prior Publication Data

US 2024/0127952 A1 Apr. 18, 2024

(30) Foreign Application Priority Data

Oct. 17, 2022 (KR) ......................... 10-2022-0133557

(51) Int. Cl.
*G16H 50/20* (2018.01)
*A61B 5/00* (2006.01)
(Continued)

(52) U.S. Cl.
CPC ........... *G16H 50/20* (2018.01); *A61B 5/4552* (2013.01); *G06T 7/0012* (2013.01); *G16H 30/40* (2018.01);
(Continued)

(58) Field of Classification Search
CPC ........ G16H 50/20; G16H 30/40; G16H 50/30; G16H 50/50; A61B 5/4552; A61B 5/00;
(Continued)

(56) References Cited

U.S. PATENT DOCUMENTS 10,460,839 B1 * 10/2019 Ricci ...................... G16H 50/20

FOREIGN PATENT DOCUMENTS

KR 10-2200999 B1 1/2021

OTHER PUBLICATIONS

Vinayahalingam, S., Xi, T., BergÃ© , S. et al. Automated detection of third molars and mandibular nerve by deep learning. Sci Rep 9, 9007 (2019). https://doi.org/10.1038/s41598-019-45487-3 (Year: 2019).*

(Continued)

*Primary Examiner* — Oneal R Mistry

*Assistant Examiner* — Rachel L Roberts

(74) *Attorney, Agent, or Firm* — Hauptman Ham, LLP

(57) ABSTRACT

The present invention provides a device including a region of interest setting unit that sets a region of interest including a third molar and a periodontal region, a parameter calculation unit that calculates at least one parameter for periodontal disease prognosis evaluation on the basis of image information within the region of interest, a tooth extraction difficulty evaluation unit that evaluates the tooth extraction difficulty for the third molar on the basis of a previously created deep learning algorithm with the parameter as an input, and a complications prediction unit that predicts complications depending on a degree of invasion between the third molar and an IAN, and the parameter calculation unit calculates a parameter among an impaction depth of the third molar, the distance between the third molar and a lower jawbone, an angle of the third molar, and the degree of invasion between the third molar and the IAN.

7 Claims, 9 Drawing Sheets

(51) Int. Cl.
  *G06T 7/00*　　　　(2017.01)
  *G16H 30/40*　　　(2018.01)
(52) U.S. Cl.
  CPC ............... *G06T 2207/10116* (2013.01); *G06T 2207/20084* (2013.01); *G06T 2207/30036* (2013.01)
(58) Field of Classification Search
  CPC ... A61B 5/0088; A61B 5/7267; A61B 6/5217; A61B 6/463; A61B 6/51; A61B 34/10; A61B 2034/105; G06T 7/0012; G06T 2207/10116; G06T 2207/20084; G06T 2207/30036; A61C 9/0046; A61C 19/04; G06N 3/08; G06V 10/25
  See application file for complete search history.

(56)　　　　　　References Cited

OTHER PUBLICATIONS

Yoo, JH., Yeom, HG., Shin, W. et al. Deep learning based prediction of extraction difficulty for mandibular third molars. Sci Rep 11, 1954 (2021). https://doi.org/10.1038/s41598-021-81449-4 (Year: 2021).*

Kim, B.S.; Yeom, H.G.; Lee, J.H.; Shin, W.S.; Yun, J.P.; Jeong, S.H.; Kang, J.H.; Kim, S.W.; Kim, B.C. Deep Learning-Based Prediction of Paresthesia after Third Molar Extraction: A Preliminary Study. Diagnostics 2021, 11, 1572. https://doi.org/10.3390/diagnostics11091572 (Year: 2021).*

Office Action dated May 30, 2024 for corresponding Korean Patent Application No. 10-2022-0133557, along with an English machine translation (16 pages).

Jeong-Hun Yoo et al., "Deep learning based prediction of extraction difficulty for mandibular third molars", Scientific Reports 11, 1954 (2021), Jan. 21, 2021 (9 pages), cited in NPL No. 1.

Waseem Jerjes et al., "Inferior alveolar nerve injury and surgical difficulty prediction in third molar surgery: The role of dental panoramic tomography", University College London Hospitals, The Journal of Clinical Dentistry, vol. XVII, No. 5, Feb. 2006 (10 pages), cited in NPL No. 1.

Maung Maung Latt et al., "Prediction of difficulty in impacted lower third molars extraction; review literature", Mahidol Dental Journal, vol. 35, No. 3, Sep.-Dec. 2015, pp. 281-290, cited in NPL No. 1.

[Supportive Materials for Exception to Loss of Novelty] Lee et al., "Automated Prediction of Extraction Difficulty and Inferior Alveolar Nerve Injury for Mandibular Third Molar Using a Deep Neural Network," Applied Sciences, Jan. 4, 2022, vol. 12 (12 pages).

* cited by examiner

Third molar detection

Setting of region of interest

Classification of tooth extraction difficulty

Prediction of likelihood of complications

38        #48

Third molar region image

Vertical                    Distoangular

Horizontal                  Mesioangular

Transverse                  Inverted

N.1                    N.2                    N.3

1

TOOTH EXTRACTION DIFFICULTY DIAGNOSIS AND COMPLICATIONS PREDICTION DEVICE AND METHOD

CROSS REFERENCE TO RELATED APPLICATION

The present application claims priority to Korean Patent Application No. 10-2022-0133557, filed Oct. 17, 2022, the entire contents of which is incorporated herein for all purposes by this reference.

TECHNICAL FIELD

The present invention relates to a tooth extraction difficulty diagnosis and complications prediction device and method, and specifically, to a device and method for automatically detecting wisdom teeth which are third molars of a lower jawbone in a panoramic radiological image, diagnosing the difficulty of tooth extraction, and predicting complications due to damage to inferior alveolar nerves.

BACKGROUND

Recently, deep learning has been applied to various fields with the goal of automation, and the field is growing rapidly. In particular, the deep learning is frequently applied to a medical field and shows high performance. The deep learning is widely used to predict and diagnose diseases through image data such as MRI and CT images and signal data such as EEG. The deep learning can also be applied to a dental field for automatic diagnosis of various diseases. This has been applied to many studies, such as classifying cystic lesions in a cone beam computed tomography (CBCT) image and estimating an age of a person through this.

Most people are born with a third molar of a lower jaw and remove the molar for a variety of reasons.

Therefore, extraction of the third molar of the lower jaw is a frequent operation in oral and maxillofacial surgery. According to a type of third molar impact, a rate of symptom development is 30 to 68% after the third molar extraction. Third molars of the lower jaw have various impaction patterns because third molars grow in various positions and directions. Therefore, it is important to ascertain the pattern of the impacted third molar of the lower jaw before tooth extraction and apply an appropriate surgical method according to an impaction pattern. There are several criteria for defining the impaction pattern of the third molar of the lower jaw. In specific impaction patterns, various problems may occur after tooth extraction.

Complications may occur after tooth extraction depending on impaction patterns of the third molar of the lower jaw. According to several studies, damage to an inferior alveolar nerve (IAN) is known to be the most common complications that occurs after the third molar of the lower jaw is removed. IAN damage may cause several paralytic symptoms in the lower jawbone, and it is most important to predict potential complications because of conflicting report results on effects of proposed surgical treatment approaches. The complications may be predicted through a relationship between the third molar of the lower jaw and the IAN, and a likelihood of the IAN damage is high when the third molar of the lower jaw comes into contact with the IAN.

A doctor should plan a surgical procedure for a patient and consider potential complications, such as IAN damage before third molar extraction, and it is essential to predict the difficulty of the tooth extraction and a likelihood of IAN damage in advance to minimize the IAN damage which is complications that may occur after tooth extraction that requires gum incision, tooth incision, and fracture.

There is a need to propose a device and method for predicting the difficulty of extraction of a third molar of a lower jaw and a likelihood of IAN damage using a deep neural network by utilizing a panoramic radiological image.

SUMMARY

An object of the present invention is to propose a device and method for predicting the difficulty of extraction of a third molar of a lower jaw and a likelihood of IAN damage using a deep neural network by utilizing a panoramic radiological image to solve the above problems.

The present invention can be implemented in various ways, including a device (system), a method, a computer program stored in a computer-readable medium, or a computer-readable medium having the computer program stored therein.

A tooth image-based tooth extraction difficulty diagnosis and complications prediction device according to an embodiment of the present invention includes a region of interest setting unit configured to set a region of interest including a third molar and a periodontal region on the basis of boundaries of a plurality of teeth; a parameter calculation unit configured to calculate at least one parameter for periodontal disease prognosis evaluation on the basis of image information within the region of interest; a tooth extraction difficulty evaluation unit configured to evaluate the tooth extraction difficulty for the third molar on the basis of a previously created deep learning algorithm with the parameter as an input; and a complications prediction unit configured to predict complications depending on a degree of invasion between the third molar and an IAN, wherein the parameter calculation unit calculates at least one parameter among an impaction depth of the third molar, the distance between the third molar and a lower jawbone, an angle of the third molar, and the degree of invasion between the third molar and the IAN.

According to an embodiment of the present invention, the tooth extraction difficulty evaluation unit combines the impaction depth of the third molar, the distance between the third molar and the lower jawbone, and the angle of the third molar to evaluate tooth extraction difficulty using one of vertical eruption (VE), soft tissue impaction (STI), partial bony impaction (PBI), and complete bony impaction (CBI).

According to an embodiment of the present invention, the complications prediction unit classifies complications prediction results into three classes depending on a degree of invasion between the third molar and the IAN.

According to an embodiment of the present invention, the tooth extraction difficulty diagnosis and complications prediction device further includes: a result output unit configured to display the difficulty of the extraction of the third molar, an extraction method, and a level of a likelihood of occurrence of the complications together with performance of detection of the third molar while overlapping these on a third molar image.

A tooth extraction difficulty diagnosis and complications prediction method according to an embodiment of the present invention includes setting a region of interest of a third molar including a periodontal region; calculating at least one parameter for tooth extraction difficulty diagnosis and complications prediction on the basis of image information within the region of interest; evaluating the tooth extraction difficulty by combining an impaction depth of the third molar, a distance between the third molar and a lower jawbone, and an angle of the third molar on the basis of a deep learning algorithm with the parameter as an input; and classifying the complications into three classes depending on the degree of invasion between the third molar and an IAN, wherein the parameter is at least one of the impaction depth of the third molar, the distance between the third molar and the lower jawbone, the angle of the third molar, and the degree of invasion between the third molar and the IAN.

According to an embodiment of the present invention, the evaluating of the tooth extraction difficulty includes combining the impaction depth of the third molar, the distance between the third molar and the lower jawbone, and the angle of the third molar to evaluate tooth extraction difficulty using one of vertical eruption (VE), soft tissue impaction (STI), partial bony impaction (PBI), and complete bony impaction (CBI).

The tooth extraction difficulty diagnosis and complications prediction method according to an embodiment of the present invention further includes: displaying the difficulty of the extraction of the third molar, an extraction method, and a level of a likelihood of occurrence of the complications together with performance of detection of the third molar while overlapping these on a third molar image.

According to the present invention, the following effects are achieved.

The present invention can also improve the efficiency and accuracy of third molar extraction diagnosis using deep learning.

Further, the present invention supports clinicians by a deep neural network automatically predicting both the difficulty of tooth extraction of the third molar of the lower jaw and the likelihood of the IAN damage due to tooth extraction through deep learning in a panoramic radiological image, thereby reducing diagnostic time and effort.

The effects of the present invention are not limited to the effects mentioned above, and other effects not mentioned will be clearly understood by those skilled in the art in the technical field to which the present invention pertains (referred to as "those skilled in the art") from the description of the claims.

BRIEF DESCRIPTION OF THE DRAWINGS

Embodiments of the present invention will be described with reference to the accompanying drawings described hereinafter, in which like reference numerals represent like elements, but the present invention is not limited thereto.

Figure 8:
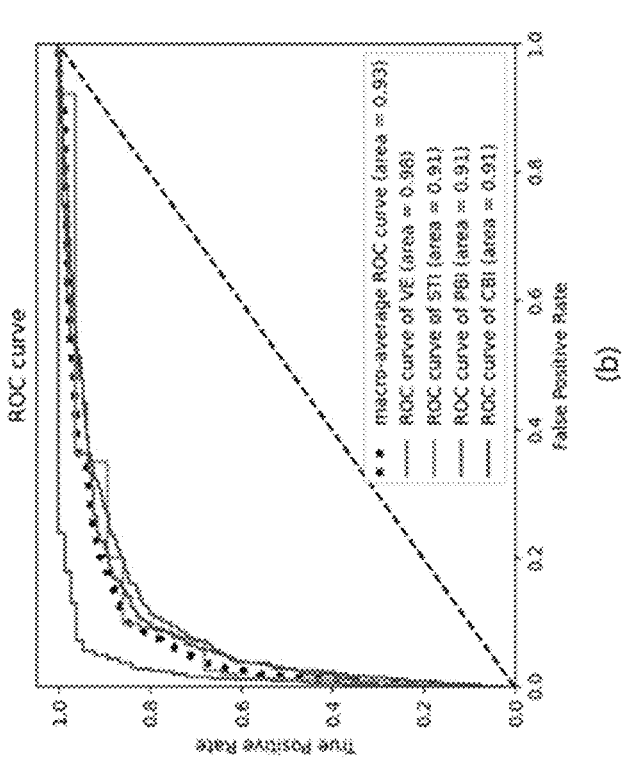
Figure 8:
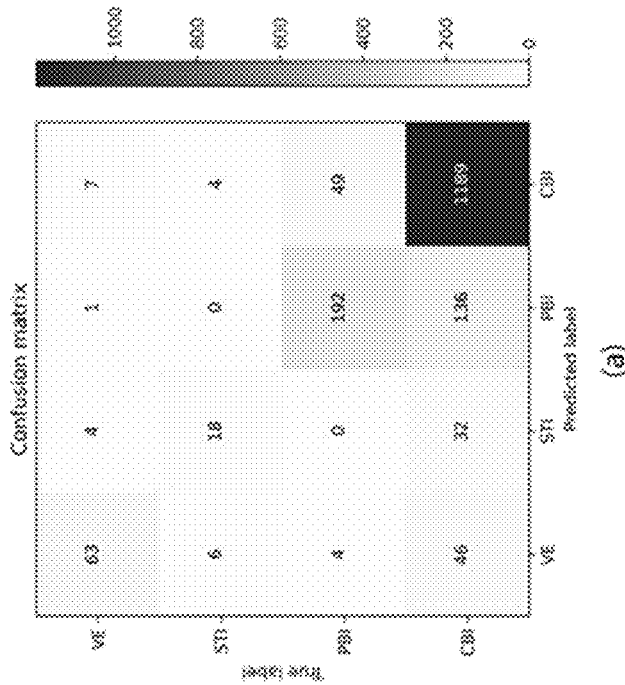

(a) of FIG. 8 is a diagram illustrating a confusion matrix of a predicted label and a true label for tooth extraction difficulty.

(b) of FIG. 8 is an ROC graph showing the performance of tooth extraction difficulty in relation to an incorrectly classified positive rate and a true positive rate of tooth extraction difficulty.

Figure 9:
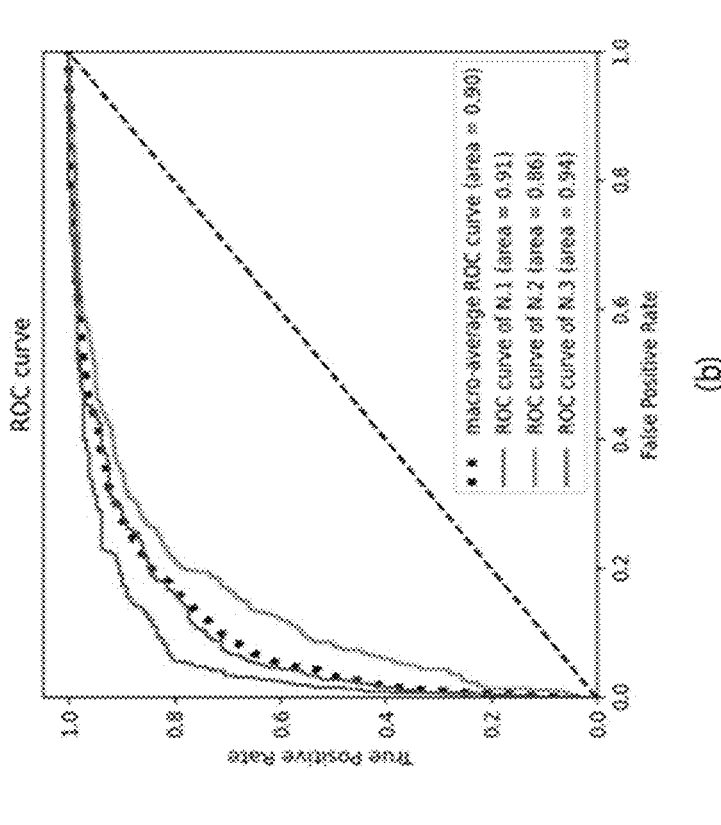
Figure 9:
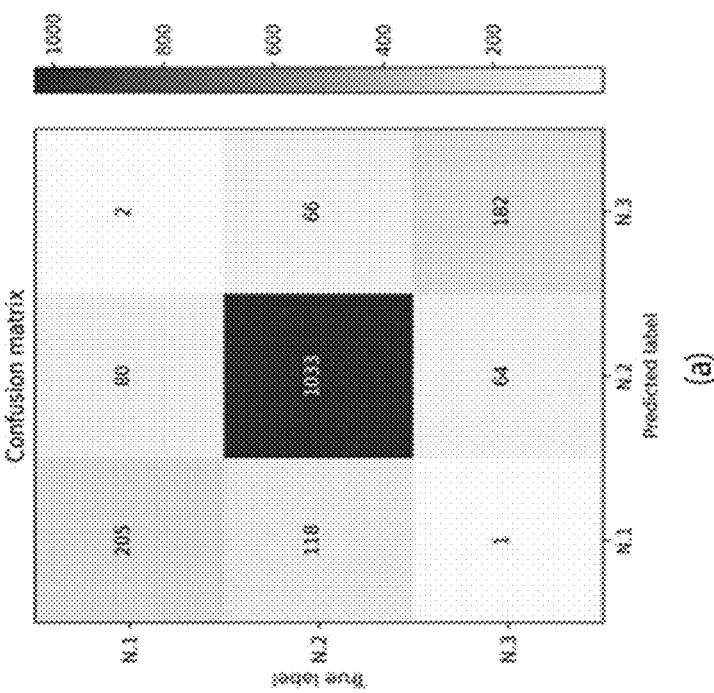

(a) of FIG. 9 is a diagram illustrating a confusion matrix of a predicted label and a true label of a likelihood of IAN damage as a likelihood of occurrence of complications.

(b) of FIG. 9 is an ROC graph showing performance of tooth extraction difficulty in relation to an incorrectly classified positive rate and a true positive rate of the likelihood of the IAN damage as the likelihood of the occurrence of the complications.

Figure 10:
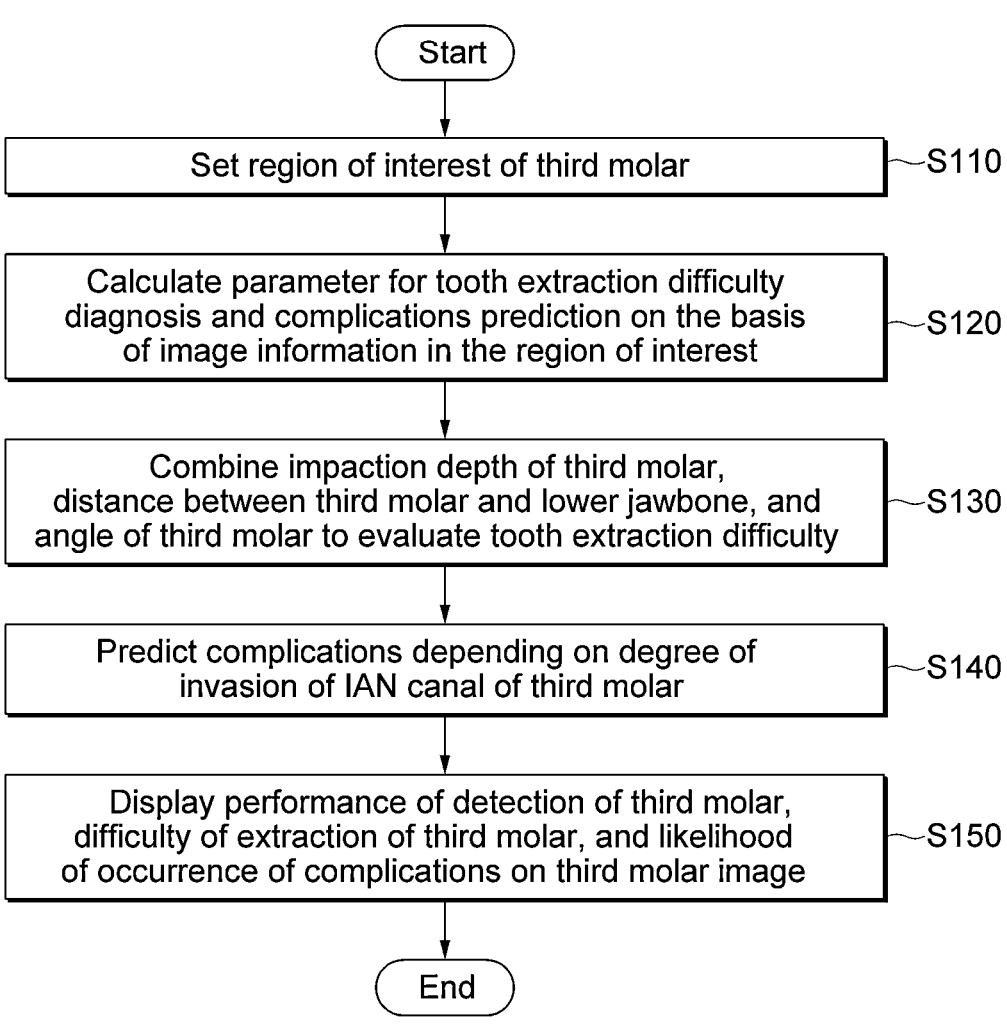

FIG. 10 is an operation flowchart of a tooth extraction difficulty diagnosis and complications prediction method according to an embodiment of the present invention.

DETAILED DESCRIPTION

Hereinafter, specific details for implementing the present invention will be described in detail with reference to the attached drawings. However, in the following description, detailed description of well-known functions or configurations will be omitted when there is concern that the gist of the present invention is unnecessarily obscured.

In the accompanying drawings, the same or corresponding components are denoted by the same reference numerals. Further, in the description of the following embodiments, repeated description of the same or corresponding components will be omitted. However, even when the description of the components is omitted, it is not intended that such components are not included in any embodiment.

Advantages and characteristics of the embodiments disclosed in the present specification, and methods for achieving these will become clear by referring to the embodiments described below along with the accompanying drawings. However, the present invention is not limited to the embodiments to be disclosed hereinafter and may be implemented in various different forms, and the present embodiments are only provided to fully inform those skilled in the art of the scope of the invention.

Unless otherwise defined, all terms (including technical and scientific terms) used in the present specification may be used with meanings that can be commonly understood by those skilled in the art to which the present invention pertains. Further, terms defined in commonly used dictionaries are not to be interpreted ideally or excessively unless clearly specifically defined.

For example, the term "technology" may refer to a system, method, computer-readable instructions, module, algorithm, hardware logic, and/or operation permitted by the above-described context and throughout the document.

Terms used in the present specification will be briefly described, and the disclosed embodiments will be described in detail. The terms used in the present specification are general terms that are currently widely used as much as possible in consideration of functions in the present invention, but the terms may vary depending on the intention of a technician working in the related field, precedents, or the emergence of new technologies. Further, there are terms arbitrarily selected by the applicant in specific cases, and in this case, the meaning thereof will be described in detail in a relevant description part of the invention. Therefore, the terms used in the present invention should be defined on the basis of meanings of the terms and the overall content of the present invention, rather than simply names of the terms.

In the present specification, singular expressions include plural expressions unless the context clearly specifies singular expressions. Further, plural expressions include singular expressions, unless the context clearly specifies plural expressions. When it is said that a certain portion includes a certain component throughout the specification, this does not mean excluding other components, but may further include the other components unless specifically stated to the contrary.

In the present invention, terms such as 'include and 'including' may indicate the presence of features, steps, operations, elements and/or components, but such terms do not preclude the addition of one or more other functions, steps, operations, elements, components and/or combinations thereof.

In the present invention, when a specific component is referred to as being 'coupled', 'combined', 'connected', 'associated', or 'reacted' to any other component, the specific component may be directly coupled, combined, connected, associated, and/or reacted to the other component, but the present invention is not limited thereto. For example, one or more intermediate components may be present between the specific component and the other component. Further, in the present invention, "and/or" may include each of one or more listed items or a combination of at least some of the one or more items.

In the present invention, terms such as 'first' and 'second' are used to distinguish specific components from other components, and the above-described components are not limited by these terms. For example, a 'first' component may be used to refer to an element in the same or similar form as a 'second' component.

A system to be described hereinafter constitutes an embodiment and is not intended to limit the claims to any one specific operating environment. The system can be used in other environments without departing from the technical spirit and scope of the claimed gist.

Figure 1:
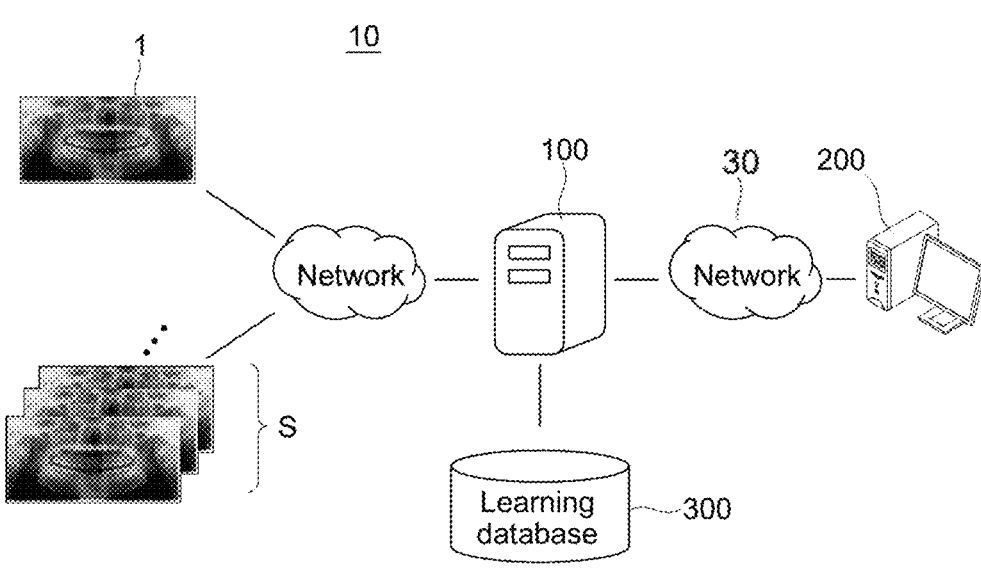
FIG. 1 is a schematic diagram of a tooth extraction difficulty diagnosis and complications prediction system according to an embodiment of the present invention.

FIG. 1 is a schematic diagram of a tooth extraction difficulty diagnosis and complications prediction system according to an embodiment of the present invention.

Referring to FIG. 1, the tooth extraction difficulty diagnosis and complications prediction system 10 according to an embodiment of the present invention includes a tooth image-based tooth extraction difficulty diagnosis and complications prediction device 100, a user terminal 200, and a learning database 300.

Further, referring to FIG. 1, the tooth image-based tooth extraction difficulty diagnosis and complications prediction device 100, the user terminal 200, and the learning database 300 may communicate with each other through a network. The network refers to a connection structure that allows information exchange between respective nodes such as terminals and servers, and examples of such a network 30 include a 3rd generation partnership project (3GPP) network, a long term evolution (LTE) network, a 5G network, a world interoperability for microwave access (WIMAX) network, the Internet, a local area network (LAN), a wireless local area network (wireless LAN), a wide area network (WAN), a personal area network (PAN), a wifi network, a Bluetooth network, a satellite broadcasting network, an analog broadcasting network, and a DMB (Digital) network but the present invention is not limited thereto.

The user terminal 200 may be, for example, any type of wireless communication device, such as a smartphone, a smart pad, a tablet PC, a personal communication system (PCS), a global system for mobile communication (GSM), a personal digital cellular (PDC), a personal handphone system (PHS), a personal digital assistant (PDA), an International Mobile Telecommunication (IMT)-2000 terminal, a Code Division Multiple Access (CDMA)-2000 terminal, a W-Code Division Multiple Access (W-CDMA) terminal, or a Wireless Broad and Internet (Wibro) terminal.

The tooth image-based tooth extraction difficulty diagnosis and complications prediction device 100 may receive a tooth image 1 to perform the tooth extraction difficulty diagnosis and complications prediction. Here, the tooth image 1 may be an image obtained by photographing all of a plurality of teeth of a target in a predetermined direction. As an example, the tooth image 1 may be an X-ray panoramic image.

According to an embodiment of the present invention, the tooth extraction difficulty diagnosis and complications prediction device 100 may be a device that receives the tooth image 1 from an imaging device such as a CT scanner, an X-ray imaging device, an ultrasound diagnostic device, and an optical scanner on the basis of an image taken by the imaging device.

According to an embodiment of the present invention, the tooth image 1 may include 5397 panoramic radiological images of a patient subjected to extraction treatment for the third molar of the lower jaw at a dental hospital. Each tooth image 1 has a resolution from a minimum of 2000×1000 to a maximum of 3000×1500 and has various levels of brightness. A dental image dataset consists of 4903 panoramic radiographic images containing 8720 images of the third molar of the lower jaw. The 8720 images of the third molar of the lower jaw are divided into training image:validation image:test image=6073:896:1751 to be input to the tooth extraction difficulty diagnosis and complications prediction device 100.

The tooth extraction difficulty diagnosis and complications prediction device 100 may detect a boundary of each of a plurality of teeth from the input tooth image 1.

Hereinafter, a process of setting a region of interest including a third molar and a periodontal region from the input tooth image and classifying tooth extraction difficulty and the likelihood of complications in the tooth extraction difficulty diagnosis and complications prediction device 100 will be described with reference to FIGS. 1 to 5.

Figure 2:
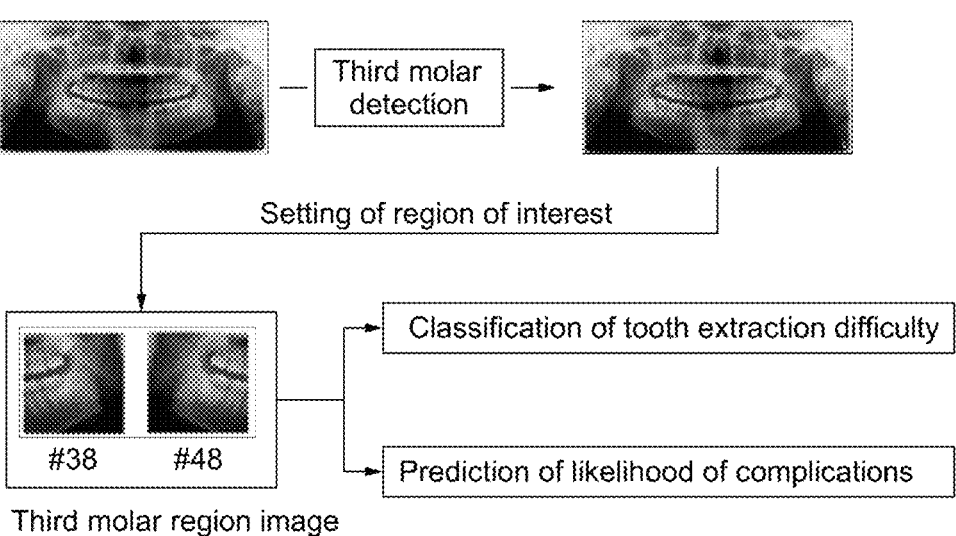
FIG. 2 is a diagram illustrating a process of setting a region of interest including a third molar and a periodontal region from an input tooth image and classifying the difficulty of tooth extraction and the likelihood of complications.
Figure 3:
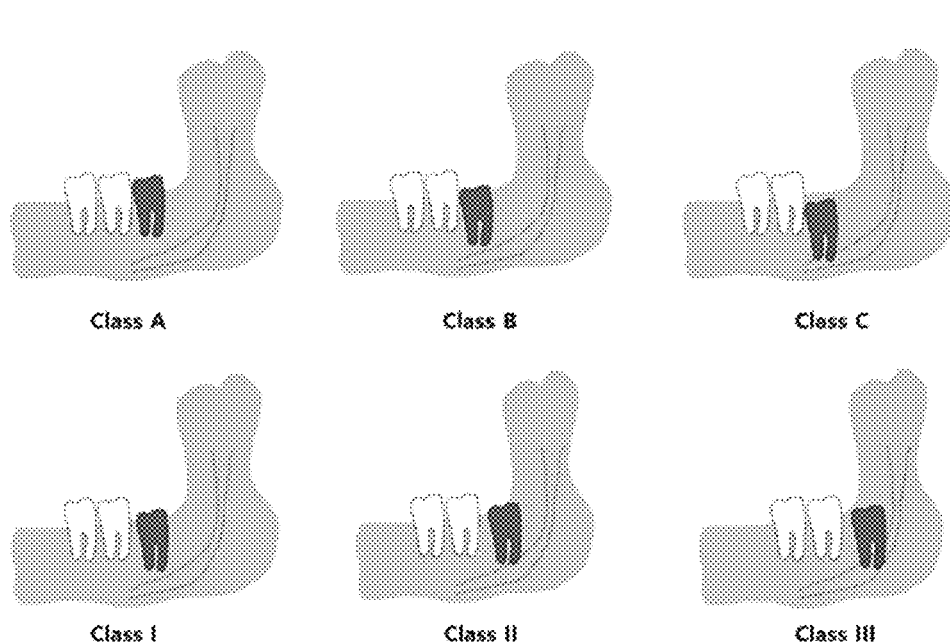
FIG. 3 is a diagram illustrating classification classes according to a height difference between the third molar and adjacent teeth and a distance between the third molar and the lower jawbone among parameters for tooth extraction difficulty evaluation of the tooth extraction difficulty diagnosis and complications prediction device according to an embodiment of the present invention.
Figure 4:
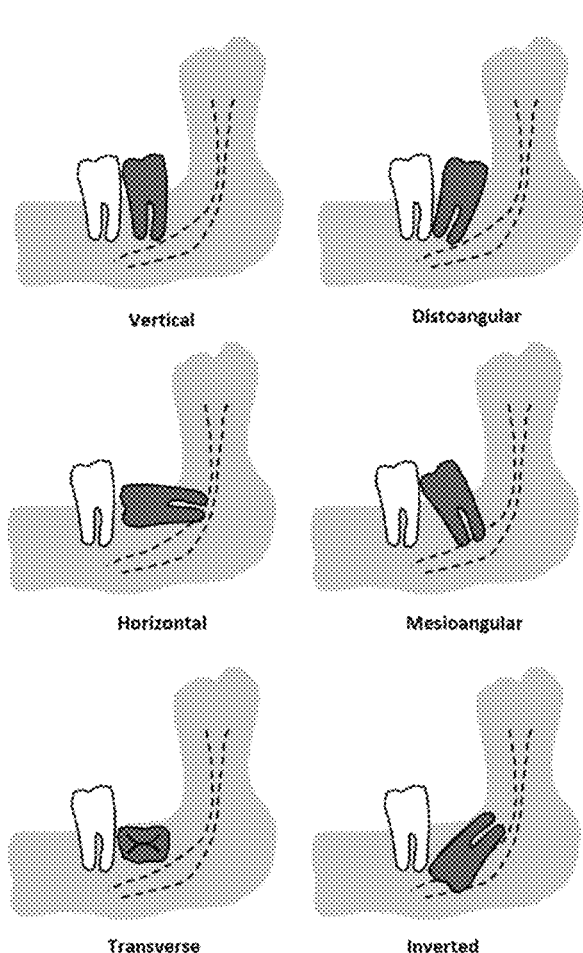
FIG. 4 is a diagram illustrating a classification class according to the angle of the third molar which is a parameter for predicting complications in the tooth extraction difficulty diagnosis and complications prediction device according to the embodiment of the present invention.
Figure 5:
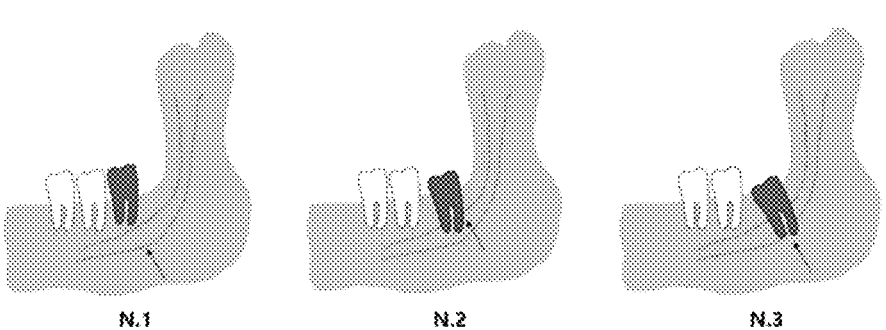
FIG. 5 is a diagram illustrating classification classes depending on a degree of invasion between the third molar and an IAN which is a parameter for predicting complications of the tooth extraction difficulty diagnosis and complications prediction device according to the embodiment of the present invention.

FIG. 2 is a diagram illustrating the process of setting a region of interest including the third molar and the periodontal region from the input tooth image and classifying the difficulty of tooth extraction and the likelihood of complications. FIG. 3 is a diagram illustrating classification classes according to a height difference between the third molar and adjacent teeth and a distance between the third molar and the lower jawbone among the parameters for tooth extraction difficulty evaluation of the tooth extraction difficulty diagnosis and complications prediction device according to an embodiment of the present invention. FIG. 4 is a diagram illustrating a classification class according to the angle of the third molar which is a parameter for predicting complications in the tooth extraction difficulty diagnosis and complications prediction device according to the embodiment of the present invention. FIG. 5 is a diagram illustrating classification classes depending on a degree of invasion between the third molars and the IAN which is a parameter for predicting complications of the tooth extraction difficulty diagnosis and complications prediction device according to the embodiment of the present invention.

Referring to FIGS. 1 and 2, the tooth extraction difficulty diagnosis and complications prediction device 100 may acquire a segmented image in which the boundary of each of the plurality of teeth is displayed more clearly from the tooth image 1. According to an embodiment of the present invention, the segmented image may be an image in which the boundary of each of the plurality of teeth is extracted and each tooth between the boundaries is displayed in a corresponding color, but the present invention is not limited thereto. For example, the color corresponding to each tooth may be determined on the basis of a type of tooth between the boundaries.

According to an embodiment of the present invention, the tooth extraction difficulty diagnosis and complications prediction device 100 may detect the boundary of each of the plurality of teeth on the basis of change in pixel brightness of the tooth image 1. For example, in an area in which the change in pixel brightness (or a differential value of pixel brightness) is equal to or greater than a preset threshold value, a tooth area and a non-tooth area may be ascertained to be distinguished, and the boundary of each of the plurality of teeth may be detected.

Further, the tooth extraction difficulty diagnosis and complications prediction device 100 may perform binarization preprocessing on the tooth image 1 before displaying the detected boundary for each tooth. Referring to FIG. 2, the binarization preprocessing may mean converting an area brighter than a set threshold value to white and a darker area to black.

Further, the tooth extraction difficulty diagnosis and complications prediction device 100 can acquire a shape of a specific tooth between the boundaries of the plurality of teeth and relative position information of the tooth to all the teeth, on the basis of a result of the binarization preprocessing.

Referring to FIG. 2, the tooth extraction difficulty diagnosis and complications prediction device 100 may extract the region of interest including the third molar and the periodontal region on the basis of the boundaries of the plurality of teeth.

The tooth extraction difficulty diagnosis and complications prediction device 100 extracts a region of interest (ROI) used as an input for classifying the tooth extraction difficulty and the likelihood of complications, such as IAN (Inferior Alveolar Nerve) damage, in a panoramic radiological image. The preprocessing is used to improve training efficiency and performance of a detection model for setting the region of interest of the third molar of the lower jaw.

First, a large-sized panoramic radiology image is resized to 1056×512 resolution and used as an input. Second, contrast limit adaptive histogram equalization (CLAHE) is applied to the panoramic radiological image to improve image contrast. Features of the deep learning model are easily extracted using histogram equalization. Retinanet can be used to detect the third molar of the lower jaw. A backbone of the detection model is ResNet-152 which is pre-trained on an ImageNet dataset. A bounding box of the third molar of the lower jaw was obtained through the detection model, was cropped to 700×700, and was suitable for inclusion of the third molar of the lower jaw, the teeth adjacent to the third molar, and the IAN in the panoramic radiographic image. The ROI created according to the bounding box is set to a tooth number (#38 and #48). These are used as inputs to a classification model for predicting the tooth extraction difficulty and the likelihood of the IAN damage. The network may be trained using a learning rate of 1e-4, batch size of 2, and focal loss. This model was trained for 250 epochs and evaluated every epoch.

According to an embodiment of the present invention, a preset figure shape for setting the region of interest may be a circular shape, but is not limited thereto and may be various shapes such as an ellipse, a rectangle, or a square. In particular, when a three-dimensional tooth image is a target, the preset figure shape may be determined to be a shape of a figure having a three-dimensional volume, such as a sphere, cylinder, polygonal column, or cube. Additionally, according to an embodiment of the present invention, the preset figure shape may be determined on the basis of at least one of type information of the tooth and position information in the overall oral structure of the tooth.

According to an embodiment of the present invention, a region of interest (RoI) is preferably determined to have a preset figure shape and to have an area or size that includes at least part of a periodontal region of a certain tooth. In the present application, the region of interest that is an image analysis target, which will be described below, is not limited to a tooth itself divided through the detected boundary between the teeth, but is set as a periodontal region including a peripheral part of the divided teeth, so that prediction of the difficulty of tooth extraction and complications can be easily performed.

Further, the tooth extraction difficulty diagnosis and complications prediction device 100 may calculate at least one parameter for evaluation of the difficulty of tooth extraction and predicting complications on the basis of image information within the region of interest.

According to an embodiment of the present invention, the parameters for the tooth extraction difficulty evaluation may include an impaction depth of the third molar, a distance between the third molar and a lower jawbone, and an angle of the third molar.

Referring to FIGS. 2 and 3, among the parameters for the tooth extraction difficulty evaluation, an impaction pattern of the third molar is classified into three classes, A, B, and C depending on a height difference between the third molar and adjacent teeth.

That is, the class A indicates a case in which a highest point of an occlusal surface of the impacted third molar of the lower jaw is at the same height as an occlusal surface of the adjacent teeth. Class B refers to a case in which the highest point of the occlusal surface of the impacted third molar of the lower jaw is between the occlusal surface of the adjacent tooth and a cervical line. Class C refers to a case in which the highest point of the impacted third molar of the lower jaw is below the cervical line of the adjacent teeth.

Referring again to FIGS. 2 and 3, among the parameters for the tooth extraction difficulty evaluation, the distance between the third molars and the lower jawbone is classified into three classes, I, II, and III depending on the distance between the third molars and the lower jawbone.

That is, Class I indicates a case in which a distance between a distal surface of the second molar of the lower jaw and a front edge of the lower jaw is larger than a width of the occlusal surface of the impacted third molar of the lower jaw. Class II indicates cases in which the distance between the distal surface of the second molar of the lower jaw and the front edge of the lower jaw is smaller than the width of the occlusal surface of the impacted third molar of the lower jaw and larger than ½. Class III indicates a case in which the distance from the distal surface of the second molar of the lower jaw and the front edge of the lower jaw bone is smaller than the width of the occlusal surface of the impacted third molar of the lower jaw.

Referring to FIGS. 2 and 4, among the parameters for the tooth extraction difficulty evaluation, the angle of the third molar is classified into six types including vertical (−10° to 10°), mesioangular (11° to 79°), horizontal (80° to 100°), distoangular (−11° to −79°), transverse (buccolingual), and inverted (−80° to 111°) with reference to the angle of the impacted third molar of the lower jaw.

According to an embodiment of the present invention, the parameters for predicting the complications include a degree of invasion between the third molars and the IAN.

Referring to FIGS. 2 and 5, the degree of invasion between the third molar and the IAN, which is a parameter for predicting complications, is classified into three classes, N.1, N.2, and N.3, depending on the degree of invasion of the IAN.

That is, N.1 indicates a case in which the third molar of the lower jaw does not reach the IAN canal in the panoramic radiographic image. In N.2, the third molar of the lower jaw invades one of the IAN canals in the panoramic radiographic image. In N.3, the third molar of the lower jaw invades two lines of the IAN canal in the panoramic radiographic image.

According to an embodiment of the present invention, the tooth extraction difficulty diagnosis and complications prediction device 100 may extract parameters including the impaction depth of the third molar, the distance between the third molar and the lower jawbone, the angle of the third molar, and the degree of invasion between the third molar and the IAN on the basis of a deep learning algorithm that has previously performed deep learning on a data set S containing a plurality of tooth images. Here, learning result data for the data set S may be stored in the learning database 300. In other words, the tooth extraction difficulty diagnosis and complications prediction device 100 may be associated with a deep learning algorithm for calculating parameters by comparing the learning result data stored in the learning database 300 with the image information in the region of interest of the received tooth image, but the present invention is not limited thereto.

Here, a deep learning algorithm for calculating parameters for tooth extraction difficulty diagnosis and complications prediction may be associated with, for example, deep learning, convolutional neural network (CNN), logistic regression, random forest, or the like, but the present invention is not limited thereto.

Figure 6:
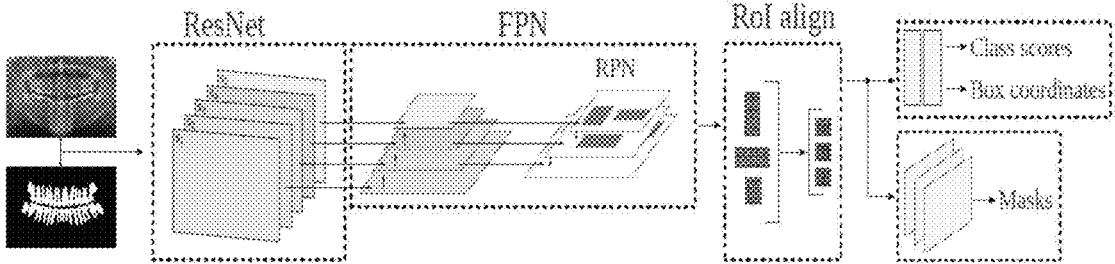
FIG. 6 is a conceptual diagram illustrating a previously created deep learning algorithm for calculating parameters for tooth extraction difficulty diagnosis and complications prediction according to an embodiment of the present invention.

FIG. 6 is a conceptual diagram illustrating the previously created deep learning algorithm for calculating the parameters for tooth extraction difficulty diagnosis and complications prediction according to an embodiment of the present invention.

Referring to FIG. 6, the tooth extraction difficulty diagnosis and complications prediction device 100 may receive, as a learning target data set, a plurality of tooth images 1 and a plurality of segmented images that correspond to the tooth images 1 and in which annotations are displayed, to generate the previously created deep learning algorithm for calculating parameters for tooth extraction difficulty diagnosis and complications prediction. The tooth extraction difficulty diagnosis and complications prediction device 100 may extract features consisting of at least 5 stages (S1 to S5) through a ResNet-152 layer, and the at least 5 stages may form a layer FPN in a pyramid network. Then, an anchor (first coordinate and second coordinate) may be determined through FPN, and a region of interest (RoI) can be determined on the basis of the anchor. Then, the tooth extraction difficulty diagnosis and complications prediction device 100 may align a plurality of determined regions of interest (RoI) and output parameter calculation results (class score) for each of the plurality of regions of interest and representative coordinates (Box coordinates) of the region of interest linked to the calculated parameter.

Further, the tooth extraction difficulty diagnosis and complications prediction device 100 may perform the tooth extraction difficulty diagnosis and complications prediction for each of the plurality of teeth on the basis of the previously created deep learning algorithm with the calculated parameter as an input. In other words, the tooth extraction difficulty diagnosis and complications prediction device 100 may first perform deep learning for an accumulated data set S for a correlation between a plurality of parameters stored in the learning database 300 and tooth extraction difficulty diagnosis and complications prediction results, such as whether or not tooth extraction is required, expected lifespan, and a probability of occurrence of a periodontal disease, and perform tooth extraction difficulty diagnosis and complications prediction for a tooth when a parameter for the tooth is newly input.

Here, the deep learning algorithm for performing the tooth extraction difficulty diagnosis and complications prediction may be associated with, for example, Deep Learning, Convolutional Neural Network (CNN), Logistic Regression, and Random Forest, or the like, but is not limited thereto.

Further, according to an embodiment of the present invention, the tooth extraction difficulty diagnosis and complications prediction device 100 may determine whether each of the plurality of teeth needs to be extracted on the basis of a previously generated deep learning algorithm. Further, as another example, performing the tooth extraction difficulty diagnosis and complications prediction may include calculating at least one of an expected lifespan of each of the plurality of teeth and the probability of the occurrence of the periodontal disease on the basis of the previously generated deep learning algorithm.

According to the embodiment, the tooth extraction difficulty diagnosis and complications prediction device 100 may simply provide a result of whether or not a tooth needs to be extracted in the form of 'tooth extraction is required' or 'tooth extraction is not required for the tooth on the basis of the calculated parameters. As another example, the tooth extraction difficulty diagnosis and complications prediction device 100 may provide the result of whether or not a tooth needs to be extracted, through conversion into numerical information of a probability of tooth extraction being required for the tooth and a probability of survival within a predetermined time range.

Figure 7:
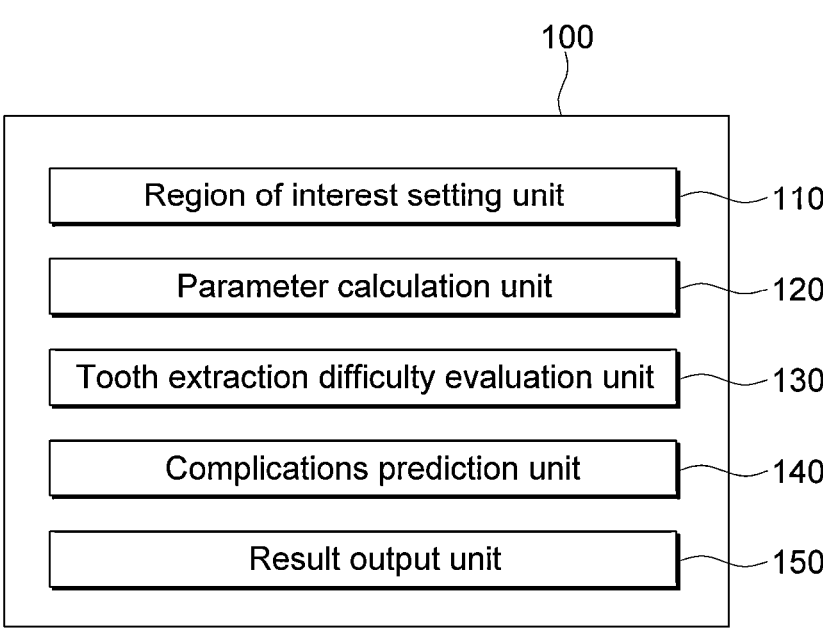
FIG. 7 is a schematic configuration diagram of a tooth image-based tooth extraction difficulty diagnosis and complications prediction device 100 according to an embodiment of the present invention.

FIG. 7 is a schematic configuration diagram of a tooth image-based tooth extraction difficulty diagnosis and complications prediction device 100 according to an embodiment of the present invention.

Referring to FIG. 7, the tooth extraction difficulty diagnosis and complications prediction device 100 may include a region of interest setting unit 110, a parameter calculation unit 120, a tooth extraction difficulty evaluation unit 130, a complications prediction unit 140, and a result output unit 150.

The region of interest setting unit 110 extracts a region of interest (ROI) used as an input for classifying the difficulty of tooth extraction and the likelihood of the IAN damage from the radiological image.

First, the large-sized panoramic radiology image is resized to 1056×512 resolution and used as an input. Second, contrast limit adaptive histogram equalization (CLAHE) is applied to the panoramic radiological image to improve image contrast. The deep learning model facilitates an extraction function by using the histogram equalization. Retinanet can be used to detect the third molar of the lower jaw. The backbone of the detection model is ResNet-152 which is pre-trained on the ImageNet dataset. The bounding box of the third molar of the lower jaw was obtained through the detection model, was cropped to 700×700, and was suitable for inclusion of the third molar of the lower jaw, the teeth adjacent to the third molar, and the IAN in the panoramic radiographic image. The ROI created according to the bounding box is set to the tooth number (#38 and #48). These are used as inputs to the classification model for predicting the tooth extraction difficulty and the likelihood of the IAN damage.

The parameter calculation unit 120 may calculate at least one parameter for the tooth extraction difficulty diagnosis and complications prediction on the basis of the image information within the region of interest. Here, the parameters for the tooth extraction difficulty diagnosis and complications prediction may include the impaction depth of the third molar, the distance between the third molar and the lower jawbone, the angle of the third molar, and the degree of invasion between the third molar and the IAN.

The tooth extraction difficulty evaluation unit 130 evaluates the tooth extraction difficulty for the third molar on the basis of the previously created deep learning algorithm with the calculated parameters as inputs.

Specifically, the tooth extraction difficulty evaluation unit 130 classifies the tooth extraction difficulty as one of vertical eruption (VE), soft tissue impaction (STI), partial bony impaction (PBI), and complete bony impaction (CBI), on the basis of the impaction depth of the third molar, the distance between the third molar and the lower jawbone, and the angle of the third molar calculated by the parameter calculation unit 120.

Referring to Table 1, the tooth extraction difficulty evaluation unit 130 combines the impaction depth of the third molar, the distance between the third molar and the lower jawbone, and the angle of the third molar to performs the evaluation through correspondence to one of four types of tooth extraction difficulties including vertical eruption (VE), soft tissue impaction (STI), partial bony impaction (PBI), and complete bony impaction (CBI).

first letter in the parameter entry indicates one of classes A, B and C regarding the depth of the impaction of the third molar, a second letter in the parameter entry indicates classes I (or 1), II (or 2) and III (or 3) regarding the distance between the third molar and the lower jawbone, and a third letter in the parameter entry indicates a first letter of six classes of the angle of the third molar of the lower jaw, including Vertical, Mesioangular, Horizontal, Distoangular, Transverse, and Inverted.

The difficulty entry indicates the difficulty of tooth extraction depending on the combination of parameters of the impaction patterns. The difficulty of the extraction of the third molar of the lower jaw is determined to train an extraction difficulty classification model. The difficulty of the tooth extraction indicated by the difficulty entry may be divided into four types depending on a surgical method for tooth extraction.

Vertical Eruption (VE) refers to a case in which a simple extraction is possible without gum incision or fracture.

Soft Tissue Impaction (STI) indicates a case in which a tooth is extracted after the gum incision.

Partial Bony Impaction (PBI) indicates a case in which tooth division is required for extraction.

Complete Bony Impaction (CBI) indicates a case in which tooth division and fracture are required when more than two-thirds of the tooth crown has been impacted.

The tooth extraction difficulty evaluation unit 130 according to an embodiment of the present invention may use R50+ViT-L/32, which is a hybrid vision transformer including ResNet-50 in ViT-Large among vision transformer models. Since the vision transformer obtains an advantage of higher resolution, resolution of an input image is 384×384. The tooth extraction difficulty evaluation unit 130 has been pre-trained using the ImageNet data set. The tooth extraction difficulty evaluation unit 130 is trained using learning rate 1e-4, batch size 8, and a cross-entropy loss function.

The complications prediction unit 140 classifies the degree of invasion between the third molar and the IAN, which is the parameter for the tooth extraction difficulty evaluation, into three classes, N1, N2, and N3 depending on the degree of invasion of the IAN according to a relationship between the third molar and the IAN canal.

That is, N.1 indicates a case in which the third molar of the lower jaw does not reach the IAN canal in the panoramic radiographic image. In N.2, the third molar of the lower jaw invades one of the IAN canals in the panoramic radiographic image. In N.3, the third molar of the lower jaw invades two lines of the IAN canal in the panoramic radiographic image.

N1 has a low likelihood of occurrence of complications due to the third molar extraction, N2 has a medium likelihood of occurrence of complications due to the third molar extraction, and N3 has a high likelihood of occurrence of complications due to the third molar extraction.

TABLE 1

| A1H | PBI | A2H | PBI | A3H | CBI | B1H | CBI | B2H | STI | B3H | CBI | C1H | CBI | C2H | CBI | C3H | CBI |
|-----|-----|-----|-----|-----|-----|-----|-----|-----|-----|-----|-----|-----|-----|-----|-----|-----|-----|
| A1M | PBI | A2M | PBI | A3M | CBI | B1M | CBI | B2M | CBI | B3M | CBI | C1M | CBI | C2M | CBI | C3M | CBI |
| A1V | VE  | A2V | STI | A3V | CBI | B1V | CBI | B2V | CBI | B3V | CBI | C1V | CBI | C2V | CBI | C3V | CBI |
| A1D | STI | A2D | PBI | A3D | CBI | B1D | CBI | B2D | CBI | B3D | CBI | C1D | CBI | C2D | CBI | C3D | CBI |
| A1I | CBI | A2I | CBI | A3I | CBI | B1I | CBI | B2I | CBI | B3I | CBI | C1I | CBI | C2I | CBI | C3I | CBI |
| A1T | PBI | A2T | CBI | A3T | CBI | B1T | STI | B2T | CBI | B3T | CBI | C1T | CBI | C2T | CBI | C3T | CBI |

A parameter entry in Table 1 indicates a combination of parameters of the impaction patterns, and an adjacent difficulty entry indicates the difficulty of the tooth extraction. A The complications prediction unit 140 may use R50+ViT-L/32, which is a hybrid vision transformer including ResNet-50 in ViT-Large among the vision transformer models, like the tooth extraction difficulty evaluation unit 130. Since the vision transformer obtains an advantage of higher resolution, the resolution of the input image is 384×384. The tooth extraction difficulty evaluation unit 130 has been pre-trained using the ImageNet data set. The tooth extraction difficulty evaluation unit 130 is trained using learning rate 1e-4, batch size 8, and a cross-entropy loss function.

The result output unit 150 may display the difficulty of the extraction of the third molar, an extraction method, and a level of the likelihood of occurrence of the complications together with the performance of detection of the third molar while overlapping these on a third molar image.

The performance of the region of interest setting unit 110 is generally evaluated through mean average precision (mAP), in which mAP predicts and calculates a correct answer when IoU>0.5, mAP[0.7] predicts and calculates the correct answer when IoU>0.7, and mAP[0.5:0.95] averages and calculates the IoU performance in a step of 0.05. Accuracy, F1-score, and AUROC were used as criteria for evaluating the performance of the region of interest setting unit 110. The accuracy is accurately calculated as a value obtained by dividing the number of predicted pieces of data by a total number of pieces of data. The F1-score is calculated using precision and recall. F1-score=2*precision*recall/precision+recall. An area under the curve of the receiver operation characteristic (AUROC) measures overall performance of all possible classification threshold values.

The performance of detection of the third molar of the region of interest setting unit 110 is displayed on the panoramic radiological image as values of mAP [0.5], mAP [0.7], and mAP=[0.5:0.95] by the result output unit 150. The performance of detection of the third molar was achieved 99.0% in mAP[0.5], 97.7% in mAP[0.7], and 85.3% in mAP[0.5:0.95], which were good results in all performance indexes.

The classification performance of the third molar extraction difficulty of the tooth extraction difficulty evaluation unit 130 was evaluated by using the accuracy, macro average of F1-score (F1-score), and the area under the curve of the receiver operation characteristic (AUROC). Referring to Table 2, a result of performing an experiment for comparing performance of a CNN of the related art with a vision transformer (R50+ViT-L/32) showed the highest classification performance across all criteria with an accuracy of the vision transformer (R50+ViT-L/32) 83.5%, F1-score 66.35%, and AUROC 92.79%.

TABLE 2

| Model | Accuracy (%) | F1-Score (%) | AUROC(%) |
|---|---|---|---|
| ResNet-34 | 80.07 | 63.28 | 91.43 |
| ResNet-152 | 82.18 | 63.23 | 91.45 |
| R50 + ViT-L/32 | 83.5 | 66.35 | 92.79 |

(a) of FIG. 8 is a diagram illustrating a confusion matrix of a predicted label and a true label for tooth extraction difficulty.

Referring to (a) of FIG. 8, PBI of about 20% of the difficulty of the tooth extraction were incorrectly classified as CBI, and CBI of about 9.7% were incorrectly classified as PBI.

(b) of FIG. 8 is an ROC graph showing the performance of tooth extraction difficulty in relation to an incorrectly classified positive rate and a true positive rate of tooth extraction difficulty.

Referring to (b) of FIG. 8, it can be seen that, with classification performance of the extraction difficulty using an ROC curve and an AUC score, a high AUC score of 91.0 to 98.0% was achieved for all the classes.

Table 3 shows evaluation results for the likelihood of the IAN damage, which is a likelihood of occurrence of complications, using the criteria of accuracy, F1-score, and AUROC. Referring to Table 3, classification performance of a vision transformer (R50+ViT-L/32) was the best, as compared to the existing CNN.

TABLE 3

| Model | Accuracy (%) | F1-Score (%) | AUROC (%) |
|---|---|---|---|
| ResNet-34 | 77.27 | 70.99 | 86.02 |
| ResNet-152 | 80.07 | 72.62 | 88.19 |
| R50 + ViT-L/32 | 81.1 | 75.55 | 90.02 |

(a) of FIG. 9 illustrates a confusion matrix for IAN damage likelihood classification using a vision transformer (R50+ViT-L/32). Referring to (a) of FIG. 8, about 27% of N.1 was incorrectly classified as N.2, and about 25% of N.3 was incorrectly classified as N.2.

(b) of FIG. 9 illustrates classification performance for the IAN damage likelihood using the ROC curve and the AUC score. Referring to (b) of FIG. 8, the IAN damage probability achieved high AUC scores of 86.0 to 94.0% for all the classes.

Hereinafter, a tooth extraction difficulty diagnosis and complications prediction device of the present invention will be briefly described on the basis of the details described above.

FIG. 10 is a diagram illustrating an exemplary flow of the tooth extraction difficulty diagnosis and complications prediction method according to an embodiment of the present invention.

The tooth image-based the tooth extraction difficulty diagnosis and complications prediction method according to an embodiment of the present application illustrated in FIG. 10 may be performed by the tooth extraction difficulty diagnosis and complications prediction device 100 described above. Therefore, the content described regarding the tooth extraction difficulty diagnosis and complications prediction device 100 can be equally applied to the description of the tooth image-based tooth extraction difficulty diagnosis and complications prediction method even when the content is omitted hereinafter.

Referring to FIG. 10, in step S110, the region of interest setting unit 110 may set the region of interest of the third molar including the periodontal region of each of the plurality of teeth on the basis of the boundary of each of the plurality of teeth.

Next, in step S120, the parameter calculation unit 120 may calculate at least one parameter for tooth extraction difficulty diagnosis and complications prediction on the basis of image information in the region of interest.

Next, in step S130, the tooth extraction difficulty evaluation unit 130 combines the impaction depth of the third molar, the distance between the third molar and the lower jawbone, and the angle of the third molar on the basis of a deep learning algorithm with the parameters as inputs, and performs the evaluation through correspondence to one of four types of tooth extraction difficulties including vertical eruption (VE), soft tissue impaction (STI), partial bony impaction (PBI), and complete bony impaction (CBI).

Next, in step S140, the complications prediction unit 140 classifies the degree of invasion between the third molar and the IAN, which is a parameter for predicting complications, into three classes including N1, N2, and N3 depending on the degree of invasion of the IAN.

Next, in step S150, the result output unit 150 displays the difficulty of the extraction of the third molar, the extraction method, and the level of the likelihood of occurrence of the complications together with the performance of detection of the third molar while overlapping these on the third molar image.

In the above description, steps S110 to S150 may be further divided into additional steps or combined into fewer steps depending on the implementation of the present disclosure. Further, some steps may be omitted or an order between steps may be changed as necessary.

The tooth image-based tooth extraction difficulty diagnosis and complications prediction method according to an embodiment of the present invention may be implemented in the form of program instructions that can be executed through various computer means and recorded on a computer-readable medium. The computer-readable medium may include program instructions, data files, data structures, or the like alone or in combination. The program instructions recorded on the medium may be particularly designed and constructed for the present invention or may be known and available to those skilled in the art of computer software. Examples of a computer-readable recording medium include magnetic media such as a hard disk, a floppy disk, and a magnetic tape, optical media such as a CD-ROM and a DVD, magneto-optical media such as a floptical disk, and hardware devices particularly configured to store and execute program instructions, such as ROM, RAM, or flash memory. Examples of the program instructions include machine language code such as code produced by a compiler, as well as high-level language code that can be executed by a computer using an interpreter or the like. The hardware devices described above may be configured to operate as one or more software modules to perform the operations of the present invention, and vice versa.

Further, the tooth image-based tooth extraction difficulty diagnosis and complications prediction method described above may also be implemented in the form of a computer program or application executed by a computer, which is stored in a recording medium.

The description of the present invention described above is for illustrative purposes, and those skilled in the art will understand that the present invention can be easily modified into other specific forms without changing the technical idea or essential characteristics of the present invention. Therefore, the embodiments described above should be understood in all respects as illustrative and not restrictive. For example, respective components described as unitary may be implemented in a distributed manner, and similarly, components described as distributed may also be implemented in a combined form.

Therefore, the spirit of the present invention should not be limited to the above-described embodiments, and the claims to be described below as well as all modifications uniformly or equivalently to the claims fall within the scope of the spirit of the present invention.

What is claimed is:

1. A tooth image-based tooth extraction difficulty diagnosis and complications prediction device, comprising:
   a region of interest setting unit configured to set a region of interest including a third molar and a periodontal region by:

resizing a panoramic radiological image to a resolution of 1056×512 pixels, applying contrast limited adaptive histogram equalization (CLAHE) to the resized image, detecting a lower third molar of the lower jaw in the panoramic radiological image by using a RetinaNet detection model having a ResNet-152 backbone, obtaining a bounding box of the lower third molar from the detection model, cropping the panoramic radiological image to 700×700 pixels based on the bounding box such that a cropped image includes the lower third molar, teeth adjacent to the lower third molar, and an inferior alveolar nerve (IAN) canal, and setting the cropped image as the region of interest;

a parameter calculation unit configured to calculate, based on image information within the region of interest, a set of parameters that comprises an impaction depth of the third molar, a distance between the third molar and a lower jawbone, an angle of the third molar, and a degree of invasion between the third molar and the IAN;

a tooth extraction difficulty evaluation unit configured to classify a tooth extraction difficulty of the third molar into one of Vertical Eruption (VE), Soft Tissue Impaction (STI), Partial Bony Impaction (PBI), and Complete Bony Impaction (CBI) by using a hybrid vision transformer model R50+ViT-L/32 as a classifier based on the impaction depth of the third molar, the distance between the third molar and the lower jawbone, and the angle of the third molar; and a complications prediction unit configured to classify a likelihood of IAN damage into three classes N1, N2, and N3 by using the hybrid vision transformer model R50+ViT-L/32 as a classifier based on the degree of invasion between the third molar and the IAN, wherein N1 indicates that the lower third molar does not reach an IAN canal in a panoramic radiographic image, N2 indicates that the lower third molar invades one IAN canal line in the panoramic radiographic image, and N3 indicates that the lower third molar invades two IAN canal lines in the panoramic radiographic image.

2. The tooth extraction difficulty diagnosis and complications prediction device of claim 1, wherein the tooth extraction difficulty evaluation unit combines the impaction depth of the third molar, the distance between the third molar and the lower jawbone, and the angle of the third molar to evaluate tooth extraction difficulty into one of vertical eruption (VE), soft tissue impaction (STI), partial bony impaction (PBI), and complete bony impaction (CBI).

3. The tooth extraction difficulty diagnosis and complications prediction device of claim 1, wherein the complications prediction unit classifies complications prediction results into three classes depending on a degree of invasion between the third molar and the IAN.

4. The tooth extraction difficulty diagnosis and complications prediction device of claim 1, further comprising:
   a result output unit configured to display the difficulty of the extraction of the third molar, an extraction method, and a level of a likelihood of occurrence of the complications together with performance of detection of the third molar while overlapping these on a third molar image.

5. A tooth image-based tooth extraction difficulty diagnosis and complications prediction method, comprising:
   setting a region of interest of a third molar including a periodontal region by:

resizing a panoramic radiological image to a resolution of 1056×512 pixels, applying contrast limited adaptive histogram equalization (CLAHE) to the resized image, detecting a lower third molar of the lower jaw in the panoramic radiological image by using a RetinaNet detection model having a ResNet-152 backbone, obtaining a bounding box of the lower third molar from the detection model, cropping the panoramic radiological image to 700×700 pixels based on the bounding box such that a cropped image includes the lower third molar, teeth adjacent to the lower third molar, and an inferior alveolar nerve (IAN) canal, and setting the cropped image as the region of interest;

calculating, based on image information within the region of interest, a set of parameters that comprises an impaction depth of the third molar, a distance between the third molar and a lower jawbone, an angle of the third molar, and a degree of invasion between the third molar and the IAN;

classifying a tooth extraction difficulty of the third molar into one of Vertical Eruption (VE), Soft Tissue Impaction (STI), Partial Bony Impaction (PBI), and Complete Bony Impaction (CBI) by using a hybrid vision transformer model R50+ViT-L/32 as a classifier based on the impaction depth of the third molar, the distance between the third molar and the lower jawbone, and the angle of the third molar; and classifying a likelihood of IAN damage into three classes N1, N2, and N3 by using the hybrid vision transformer model R50+ViT-L/32 as a classifier based on the degree of invasion between the third molar and the IAN, wherein N1 indicates that the lower third molar does not reach an IAN canal in a panoramic radiographic image, N2 indicates that the lower third molar invades one IAN canal line in the panoramic radiographic image, and N3 indicates that the lower third molar invades two IAN canal lines in the panoramic radiographic image.

6. The tooth extraction difficulty diagnosis and complications prediction method of claim 5, wherein classifying the tooth extraction difficulty includes combining the impaction depth of the third molar, the distance between the third molar and the lower jawbone, and the angle of the third molar to evaluate tooth extraction difficulty into one of vertical eruption (VE), soft tissue impaction (STI), partial bony impaction (PBI), and complete bony impaction (CBI).

7. The tooth extraction difficulty diagnosis and complications prediction method of claim 5, further comprising:

displaying the difficulty of the extraction of the third molar, an extraction method, and a level of a likelihood of occurrence of the complications together with performance of detection of the third molar while overlapping these on a third molar image.

\*  \*  \*  \*  \*